United States Patent
Gutierrez et al.

(10) Patent No.: US 11,311,373 B2
(45) Date of Patent: Apr. 26, 2022

(54) OPHTHALMIC SYSTEM INCLUDING ACCOMMODATING INTRAOCULAR LENS AND REMOTE COMPONENT AND RELATED METHODS OF USE

(71) Applicant: Verily Life Sciences LLC, South San Francisco, CA (US)

(72) Inventors: Christian Gutierrez, Pacifica, CA (US); Brooke Basinger, San Francisco, CA (US); Patricia Johnson, San Carlos, CA (US); Stein Kuiper, South San Francisco, CA (US); Kedar Shah, San Francisco, CA (US); Georges Goetz, Mountain View, CA (US); Shishira Nagesh, San Francisco, CA (US); Chelsea Gordon, San Mateo, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 131 days.

(21) Appl. No.: 16/670,921

(22) Filed: Oct. 31, 2019

(65) Prior Publication Data
US 2020/0138565 A1    May 7, 2020

Related U.S. Application Data

(60) Provisional application No. 62/755,772, filed on Nov. 5, 2018.

(51) Int. Cl.
*A61F 2/16* (2006.01)
(52) U.S. Cl.
CPC .... *A61F 2/1624* (2013.01); *A61F 2230/0065* (2013.01); *A61F 2250/0001* (2013.01)

(58) Field of Classification Search
CPC ............ A61F 2/1624; A61F 2250/0001; A61F 2250/0002
See application file for complete search history.

(56) References Cited

U.S. PATENT DOCUMENTS

| 6,312,393 B1 | 11/2001 | Abreu |
| 9,289,325 B2 | 3/2016 | Zehnder et al. |
| (Continued) |

OTHER PUBLICATIONS

International Search Report and Written Opinion dated Feb. 19, 2020 in corresponding international patent application No. PCT/US2019/059790, 11 pages.

*Primary Examiner* — Javier G Blanco
(74) *Attorney, Agent, or Firm* — Christensen O'Connor Johnson Kindness PLLC

(57) ABSTRACT

Ophthalmic systems and methods of changing an optical power of an ophthalmic system are described. In an example, the ophthalmic system includes an accommodating intraocular device shaped to be implantable in an eye and an extraocular device separate from the accommodating intraocular device shaped to be removably mountable to a portion of the eye outside a bulb of the eye, such as an underlid portion of the eye. In an example, the method includes wirelessly transmitting power from a power source of an extraocular device removably mounted outside a bulb of an eye to an accommodating intraocular device implanted in the eye. In an example, the method includes sensing with an accommodation sensor biological accommodation signals of the eye; generating accommodation control signals representative of the biological accommodation signals; and driving an accommodation actuator disposed in the accommodating intraocular device based on the accommodation control signals to change an optical power of the ophthalmic system.

10 Claims, 9 Drawing Sheets

(56) References Cited

U.S. PATENT DOCUMENTS

| | | |
|---|---|---|
| 9,331,791 B2 | 5/2016 | Liran et al. |
| 9,486,362 B2 | 11/2016 | Shikamura et al. |
| 9,700,722 B2 | 7/2017 | Zehnder et al. |
| 9,884,180 B1 | 2/2018 | Ho et al. |
| 10,076,408 B2 | 9/2018 | Basinger et al. |
| 10,117,740 B1 | 11/2018 | Lee |
| 2007/0123981 A1 | 5/2007 | Tassignon |
| 2009/0264966 A1 | 10/2009 | Blum et al. |
| 2009/0287275 A1 | 11/2009 | Suaning et al. |
| 2011/0152969 A1 | 6/2011 | Zehnder et al. |
| 2013/0184815 A1* | 7/2013 | Roholt .................. A61F 2/1635 623/6.22 |
| 2013/0194540 A1 | 8/2013 | Pugh et al. |
| 2014/0058506 A1 | 2/2014 | Tai et al. |
| 2016/0113760 A1* | 4/2016 | Conrad .................. A61F 2/1648 623/6.22 |
| 2017/0255026 A1 | 9/2017 | Rakhyani et al. |
| 2017/0367815 A1 | 12/2017 | Basinger et al. |

\* cited by examiner

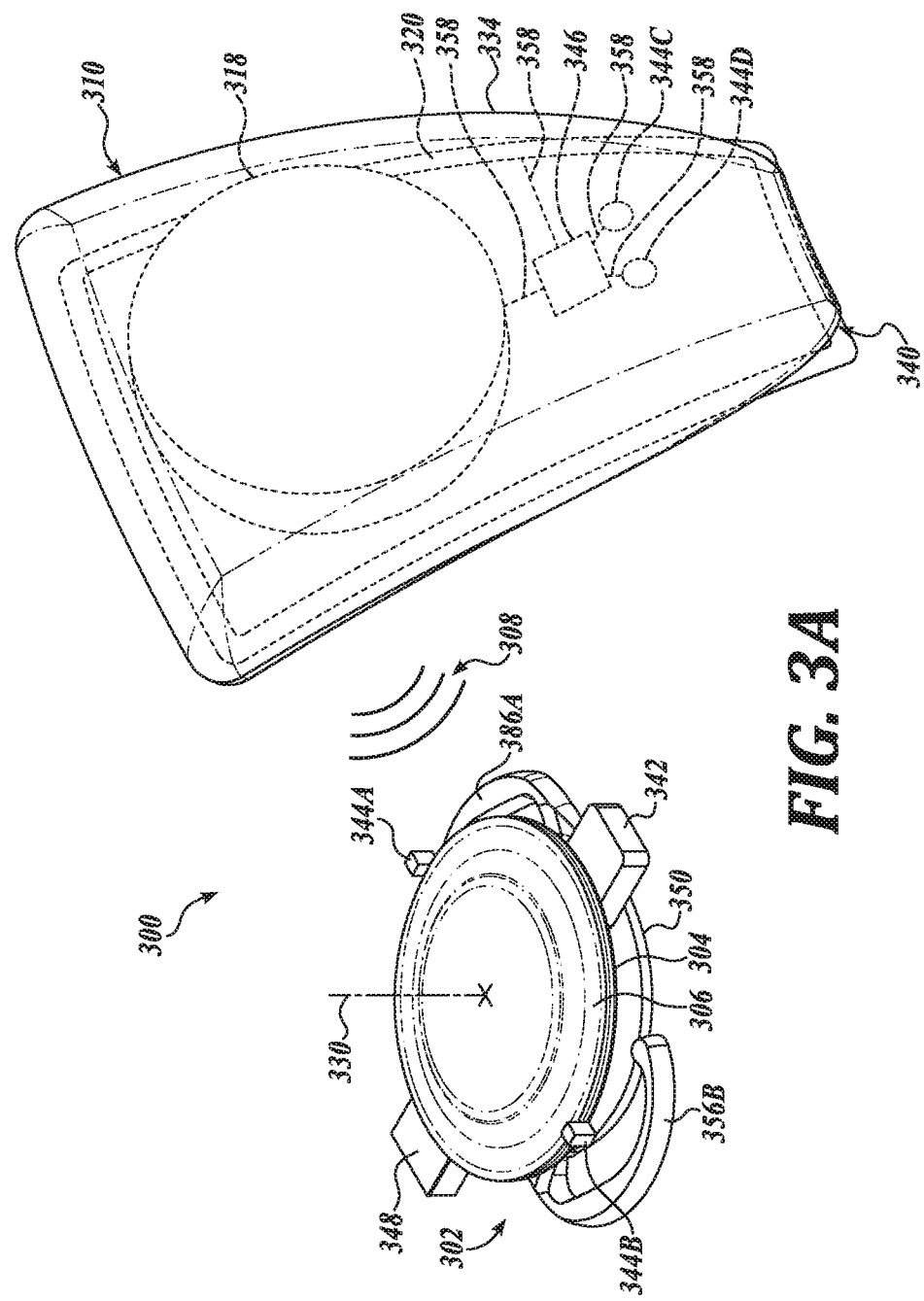

OPHTHALMIC SYSTEM INCLUDING ACCOMMODATING INTRAOCULAR LENS AND REMOTE COMPONENT AND RELATED METHODS OF USE

CROSS-REFERENCE TO RELATED APPLICATION

This application claims the benefit of U.S. Provisional Application No. 62/755,772, filed Nov. 5, 2018, which is hereby incorporated by reference in its entirety.

TECHNICAL FIELD

This disclosure relates generally to ophthalmic systems and, in particular but not exclusively, relates to accommodating ophthalmic systems.

BACKGROUND INFORMATION

Cataracts and presbyopia may be treated with implantable lenses that provide accommodation. Cataract treatment includes implantation of a replacement lens. Such lenses, which may also be referred to as intraocular lenses, may provide static accommodation, dynamic accommodation, or a combination thereof. Various techniques may be available to provide dynamic accommodation, such as mechanically or electrically controlled accommodation. The accommodation may be provided by actuation of a dynamic optical component that provides multiple levels of optical power. The change in optical power may provide different focal distances to the user via the intraocular lens. The amount of actuation, however, may depend on the technique used, e.g., mechanical or electrical. For successful treatment of presbyopia, the implanted lens may include a dynamic component.

Such accommodating implantable lenses may include a power source for powering, for example, an accommodation actuator to change an optical power of the accommodating implantable lens. Implanted batteries and other conventional implantable power sources may fail over time, requiring replacement of the implantable lens; a process that may be costly and burdensome to patients. Further, batteries in implantable accommodating lenses add bulk and reduce flexibility of implantable accommodating lenses generally leading to more invasive implantation and removal procedures.

BRIEF DESCRIPTION OF THE DRAWINGS

Non-limiting and non-exhaustive embodiments of the claimed subject matter are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIG. 3A is a perspective view of another ophthalmic system, in accordance with an embodiment of the disclosure.

DETAILED DESCRIPTION

Embodiments of an accommodating ophthalmic system including an accommodating intraocular device and a remote component and related methods of use are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

An intraocular device, such as an intraocular lens, may be implanted in a user's eye, such as within a bulb of the eye, to assist in accommodation when the user's lens is no longer able to change focus, for example. The intraocular device may have static optical power and/or may have the ability to dynamically accommodate, e.g., alter the optical power of the intraocular device, so the user may change focus similar to the natural eye. To provide dynamic accommodation, the intraocular device may include electronics, conductive traces, electrodes, and the like, coupled to an accommodation actuator configured to change an optical power of the intraocular device. The electronics may provide a voltage to the accommodation actuator via one or more conductors to cause accommodation, for example. The electronics may further include a power source, such as a battery. Such intraocular batteries may fail over time requiring replacement generally including surgical removal and re-implantation.

Additionally, because the intraocular device may be implanted into the eye, a small incision in the cornea or sclera may be desirable. Yet, because the intraocular device may be of the same size as the original lens, for example, a large incision may be required. However, if the intraocular device is capable of, for example, being rolled up into a cylindrical shape or folded, a smaller incision may be possible. In general, many of the materials forming intraocular devices may be amenable to being rolled or folded, but some intraocular power sources, such as batteries, add bulk to implantable intraocular device and, thus may require a larger incision in the eye for implantation. Such large incisions in the eye are generally more invasive and burdensome on patients.

Figure 1A:
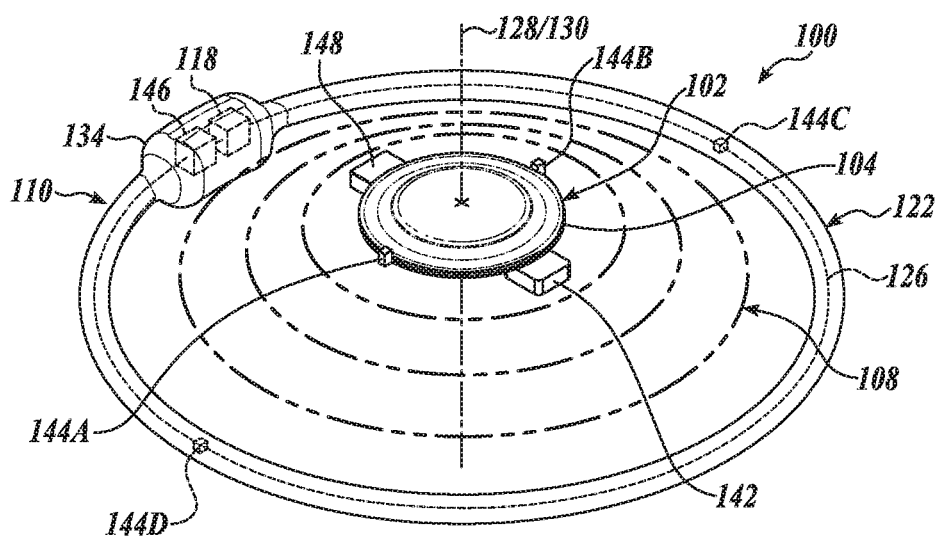
FIG. 1A is a perspective view of an ophthalmic system, in accordance with an embodiment of the disclosure.
Figure 1B:
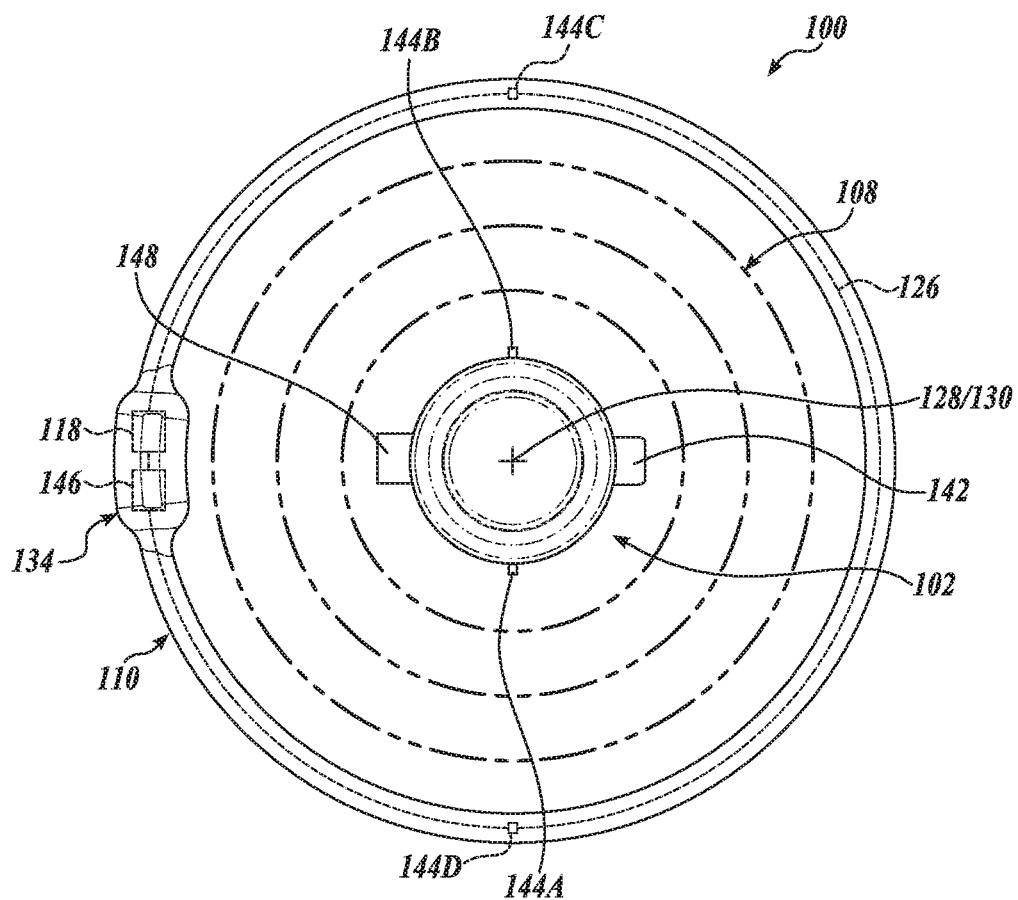
FIG. 1B is a top-down plan view of the ophthalmic system of FIG. 1A, in accordance with an embodiment of the disclosure.
Figure 1C:
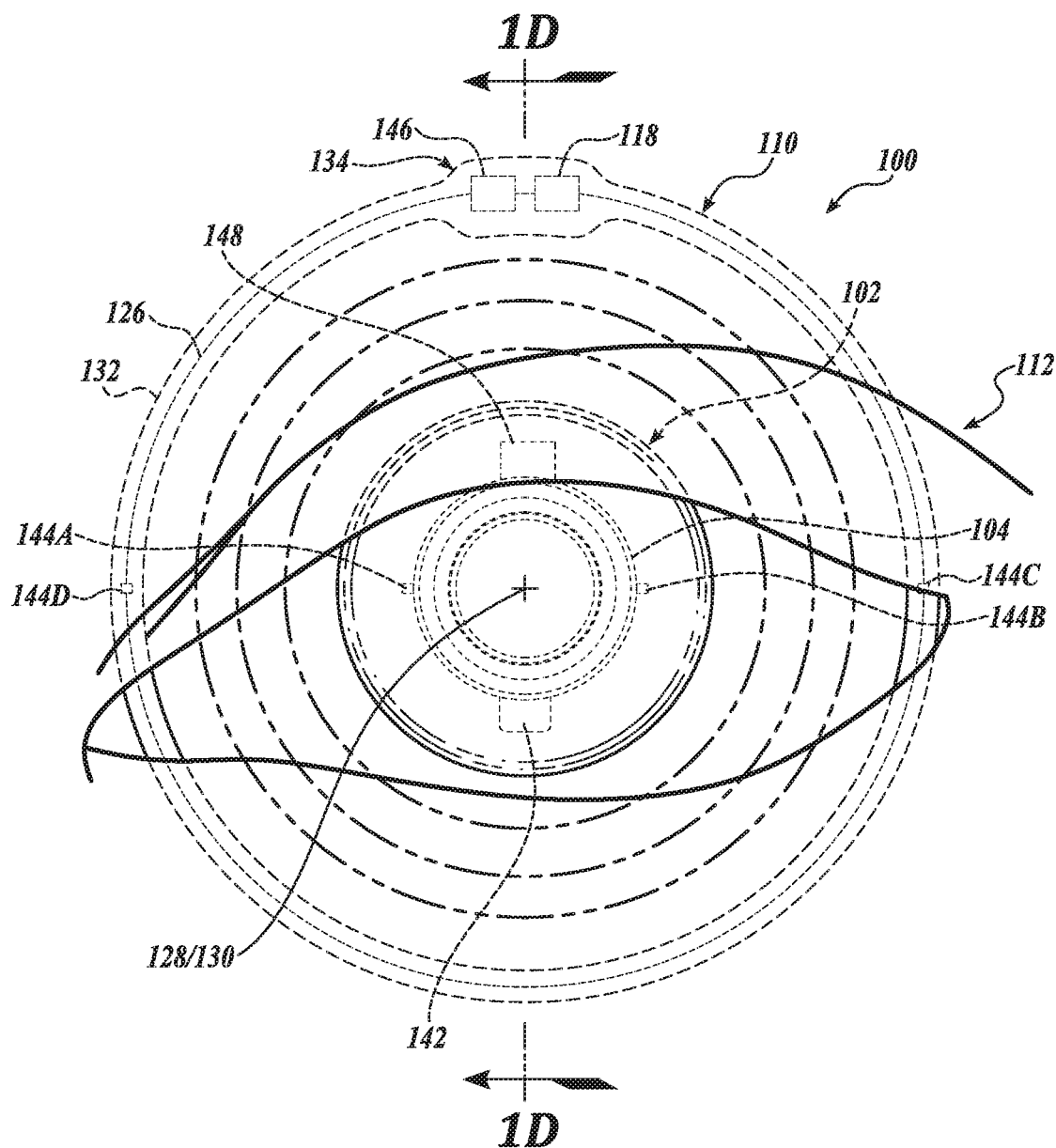
FIG. 1C is another top-down plan view of the ophthalmic system of FIG. 1A shown implanted in and mounted on an eye, in accordance with an embodiment of the disclosure.
Figure 1D:
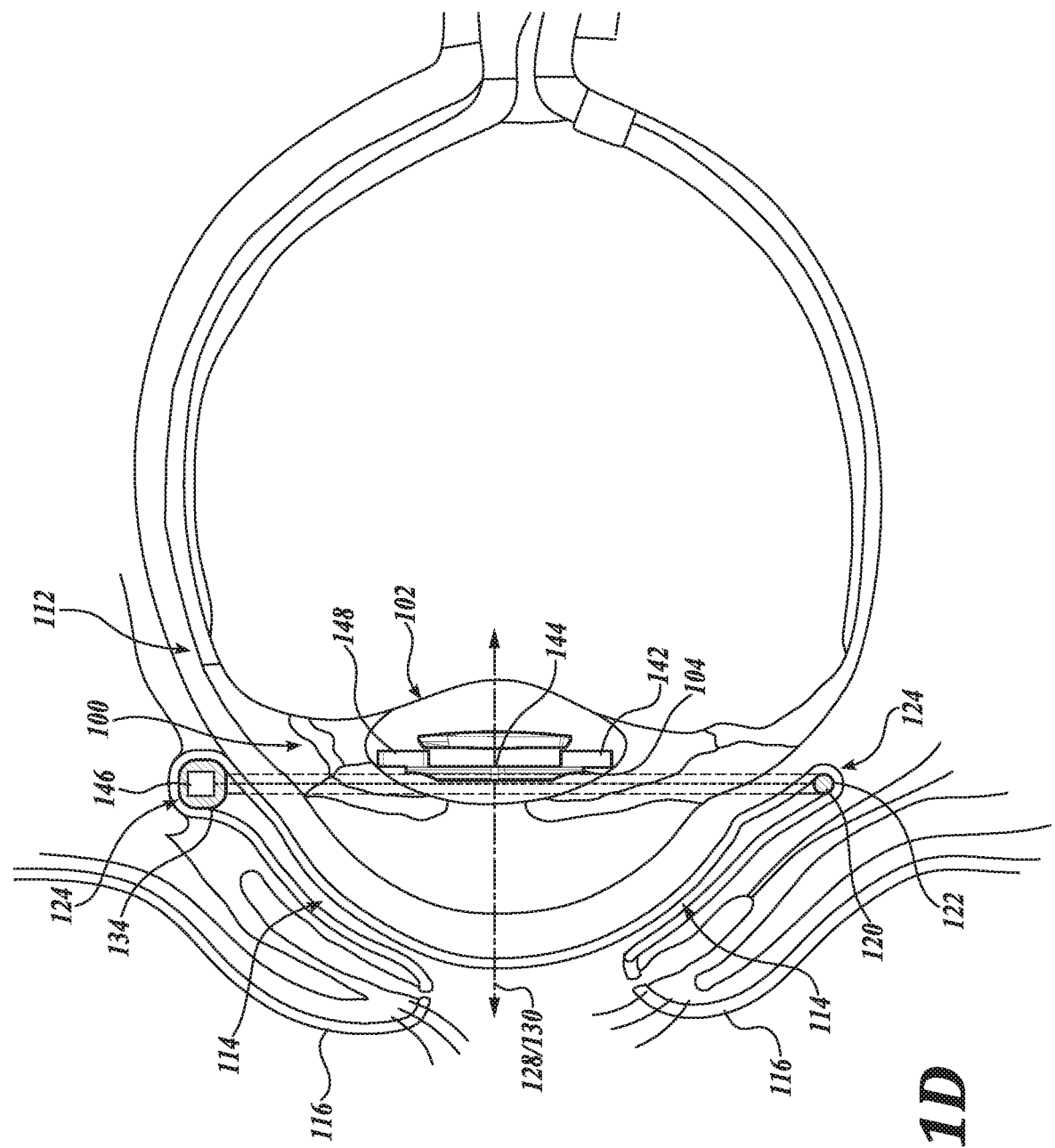
FIG. 1D is a view in cross-section of the ophthalmic system of FIG. 1A shown implanted in and mounted on an eye, in accordance with an embodiment of the disclosure.

FIG. 1A is a perspective view of an ophthalmic system 100, in accordance with an embodiment of the disclosure. FIG. 1B is a top-down plan view of the ophthalmic system 100, in accordance with an embodiment of the disclosure. FIG. 1C is another top-down plan view of the ophthalmic system 100 shown implanted in and mounted on an eye 112, in accordance with an embodiment of the disclosure. FIG. 1D is a view in cross-section of the ophthalmic system 100 shown implanted in and mounted on an eye 112, in accordance with an embodiment of the disclosure.

As shown, ophthalmic system 100 includes an accommodating intraocular device 102 and a remote device 110. As discussed further herein, the accommodating intraocular device 102 is shaped to be implantable in an eye 112, such as inside an eye 112 in a capsular bag of the eye 112. Further, accommodating intraocular device 102 is configured to provide optical accommodation, such as through dynamically changing an optical power of the accommodating intraocular device 102. Remote device 110 is physically separate from accommodating intraocular device 102. Accordingly, in an embodiment, the remote device 110 is an extraocular device 110 shaped to be mounted on an eye 112, such as in an underlid portion 114 of an eye 112, as discussed further herein with respect to FIGS. 1C and 1D. Such removable mounting does not generally include wires, cables, or other physical connection between the extraocular device 110 and accommodating intraocular device 102. In this regard, accommodating intraocular device 102 and extraocular device 110 are configured to exchange power 108 and data wirelessly. Further, the extraocular device 110 may be removably mounted and removed from an eye by a user, in some embodiments without the assistance of trained healthcare providers.

Extraocular device 110 is shown to include an extraocular power source 118; and a wireless transmitter 126 operatively coupled to the extraocular power source 118. Wireless transmitter 126 is configured to wirelessly transmit power 108 from the extraocular power source 118 for receipt by a wireless receiver 104 of the accommodating intraocular device 102. In this regard, power storage requirements of the ophthalmic system 100 may be satisfied, in some embodiments, by the extraocular device 110. Accordingly, in an embodiment, accommodating intraocular device 102 is free of a battery or other bulky, inflexible intraocular power sources. As discussed further herein, such intraocular power sources tend to be bulky and inflexible making implantation and eventual removal burdensome on patients. Without a battery disposed in the accommodating intraocular device 102 implanting incisions in the eye may be smaller. Further, without a battery disposed in the accommodating intraocular device 102 intervals between implantation and replacement may generally be longer. In one embodiment, intraocular device 102 includes a battery (not shown), such as a battery configured to power electronics of the intraocular device 102 and to receive power from extraocular device 110.

Extraocular power source 118 can include a battery. In an embodiment, extraocular power source 118 is a primary battery. In that regard, extraocular device 110 may be disposable, such as after extraocular power source 118 runs out of power. In an embodiment, extraocular power source 118 includes a secondary cell. In that regard, the power source of extraocular device 110 may be recharged after use. Further, wireless transmitter 126 may be a transceiver configured to wirelessly receive power from another wireless power source (see FIGS. 3A-3C). In an embodiment, the extraocular power source 118 is semi-toroidal (not shown) and shaped to be disposed in a space between an eyelid 116 and sclera of an eye 112. In an embodiment, extraocular power source 118 includes components chosen from a lithium-ion battery, an array of supercapacitors, an array of solid-state batteries, and combinations thereof.

In an embodiment, the extraocular device 110 is shaped to be removably mountable to an underlid portion 114 of the eye 112 disposed under an eyelid 116. In this regard, the extraocular device 110 may be securely but removably mounted onto a portion of a body of a user proximate to the accommodating intraocular device 102 when implanted in an eye 112. Such proximity is generally suitable, for example, for transmission of power 108 and/or data from the extraocular device 110 to the accommodating intraocular device 102.

In the illustrated embodiment, the extraocular device 110 comprises a ring-shaped structure 122. Such a ring-shaped structure 122 is shaped to encircle a periocular space 124 of the eye 112 outside of the limbus of the eye 112 when the extraocular device 110 is removably mounted to the underlid portion 114 of the eye 112. See, for example, FIGS. 1C and 1D. In an embodiment, the extraocular device 110 is shaped such that it does not extend over a pupil of an eye when removably mounted thereon. In an embodiment, extraocular device 110 is shaped to be mounted on a portion outside of outside of a fibrous tunic of an eye. In this regard, the extraocular device 110 is shaped to be disposed outside of a bulb of the eye. As discussed further herein, implantation of devices inside a bulb of an eye can be expensive and burdensome of patients. By mounting the extraocular device 110 outside of a bulb of the eye 112, such as in a periocular space of the eye, such burden and cost may be avoided. In an embodiment, the ring-shaped structure 122 has, for example, a diameter of about 25 mm and a thickness of about 1 mm suitable for mounting to the periocular space 124 of the eye 112. Because the extraocular device 110 is removably mountable to an underlid portion 114 of the eye 112 disposed under an eyelid 116, such as a periocular space 124 of an eye 112 outside of a cornea of the eye 112 and on top of conjunctiva 138 of the eye 112, a user may remove the extraocular device 110 when the extraocular power source 118 is depleted or when the extraocular device 110 is in need of cleaning. Such mounting and removal of the extraocular device 110 to and from the periocular space 124 of the eye 112 can be performed, for example, by a user and without assistance from a trained healthcare provider, such as a surgeon, an ophthalmologist, or an optometrist.

The ring-shaped structure 122 of the extraocular device 110 may house the wireless transmitter 126 including, in the illustrated embodiment, an extraocular antenna disposed within the ring-shaped structure 122. In an embodiment, the extraocular antenna is a multi-turn antenna, such as a multi-turn antenna having a number of turns with thicknesses of approximately 10 µm. The wireless transmitter 126 including the extraocular antenna may include a shape memory alloy, such as nitinol, to improve wearability and structural support for the ring-shaped structure 122. The shape memory alloy may further be ferrous to enhance wireless coupling between the wireless transmitter 126 and the wireless receiver 104 of the accommodating intraocular device 102.

As shown, the wireless transmitter 126 has a first central axis 128. The extraocular device 110 is positionable, for example, when the extraocular device 110 is removably mounted to a periocular space 124 of the eye 112, such that a second central axis 130 of an intraocular antenna of the wireless receiver 104 is substantially coaxial, such as in a range of about 20° to about 30°, with the first central axis 128, such as when the accommodating intraocular device 102 is implanted in the eye 112. See, for example, FIGS. 1C and 1D. As shown, first central axis 128 and second central axis 130 are coaxial when intraocular device 102 is mounted in and extraocular device 110 is mounted on the eye 112 and eye 112 is in a resting position. In this regard, the ophthalmic system 100 is shaped and positionable to affect efficient power 108 and/or signal transfer from the extraocular device 110 to the accommodating intraocular device 102. Such an arrangement can also accommodate power 108 and/or signal transfer with a misalignment between the first central axis 128 and the second central axis 130 in a range of, for example, about 20° to about 30°. In this regard, as the eye 112 moves to change a direction of gaze, the ophthalmic system 100 is configured to affect efficient power 108 and/or signal transfer from the extraocular device 110 as the direction of gaze of the eye 112 changes.

Portions of the extraocular device 110, such as those shaped to contact a portion of the body onto which it is mounted, may include materials configured to increase comfort for the user. In that regard, portions of the extraocular device 110, such as the ring-shaped structure 122, and the housing 134 may include a material chosen from a hydrogel layer, HEMA, polyethylene glycol, and combinations thereof.

Extraocular device 110 may include an extraocular controller 146. In the illustrated embodiment, the extraocular device 110 includes a housing 134 disposed on a portion of the ring-shaped structure 122. In an embodiment, the extraocular power source 118 and/or an extraocular controller 146 are disposed within the housing 134. In that regard, the extraocular controller 146 may be operably coupled to the wireless transmitter 126 and the extraocular power source 118. In an embodiment, the extraocular controller 146 includes logic that when executed by the extraocular controller 146 causes the ophthalmic system 100 to perform operations. Such operations can include, for example, transmitting, with the wireless transmitter 126, power 108, in the form of, for example, radio-frequency electromagnetic radiation for receipt by the wireless receiver 104.

As above, ophthalmic system 100 includes an accommodating intraocular device 102. Accommodating intraocular device 102 is shown to include a wireless receiver 104 suitable to wirelessly receive power 108, such as radio-frequency power 108 from extraocular device 110. In an embodiment, wireless receiver 104 is a wireless antenna disposed within the accommodating intraocular device 102. In an embodiment, voltage-carrying electrical traces of the accommodating intraocular device 102, such as wireless antenna are made of or coated with a valve metal, such as titanium, and embedded in or coated with an ion-permeable layer, such as silicone. Such configurations generally prevent or slow corrosion and electrolysis of the electrical traces. In another embodiment, the electrical traces of the accommodating intraocular device 102 are coated or covered with alternating layers of dielectric and polymer barrier coatings. In an embodiment, some electronic components of the accommodating intraocular device 102, such as the intraocular controller 142, are disposed in a hermetically sealed package, such as a laser-sealed glass container including titanium feeds (not shown).

Accommodating intraocular device 102 is shown to further include sensors 144A and 144B configured to detect biological accommodation signals of the eye 112. As discussed further herein with respect to method 500 and FIGS. 2A-2C, in some embodiments, accommodating intraocular device 102 includes one or more sensors 144A and 144B configured to detect biological accommodation signals of the eye 112. As discussed further herein, such biological accommodation signals can include a position or velocity of ciliary muscles of the eye 112, electrical activity of ciliary muscles of the eye 112, and a direction of gaze of the eye 112.

In the illustrated embodiment, accommodating intraocular device 102 includes two sensors 144A and 144B disposed on opposing sides of accommodating intraocular device 102. In this regard, sensors 144A and 144B are configured to sense biological accommodating signals, such as positions of ciliary muscles of the eye, on different sides of the eye. Such sensing may be useful in detecting a target accommodation state of an eye or a direction of gaze of an eye 112.

Figure 3B:
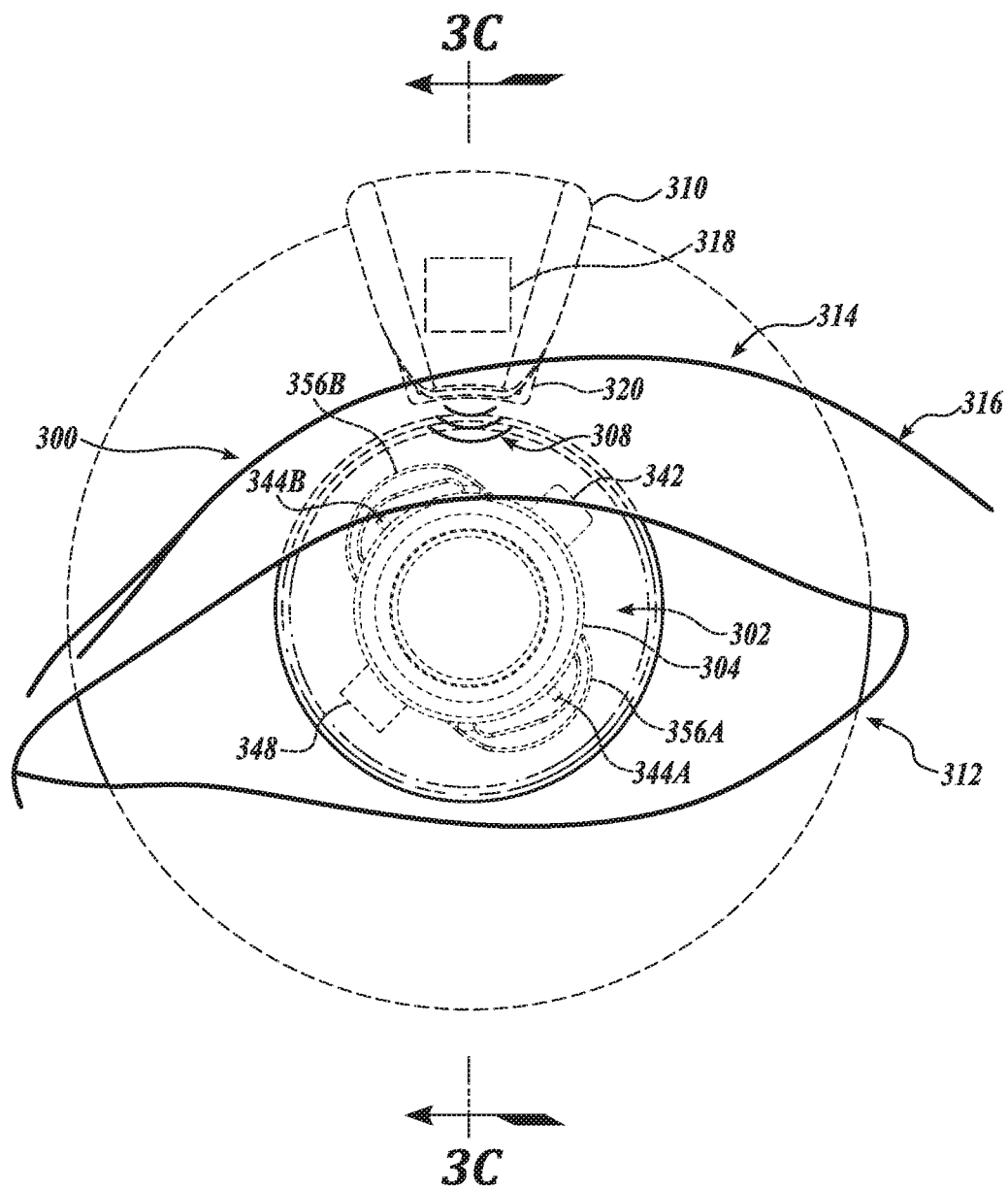
FIG. 3B is a top-down plan view of the ophthalmic system of FIG. 3A shown implanted in and mounted on an eye, in accordance with an embodiment of the disclosure.
Figure 3C:
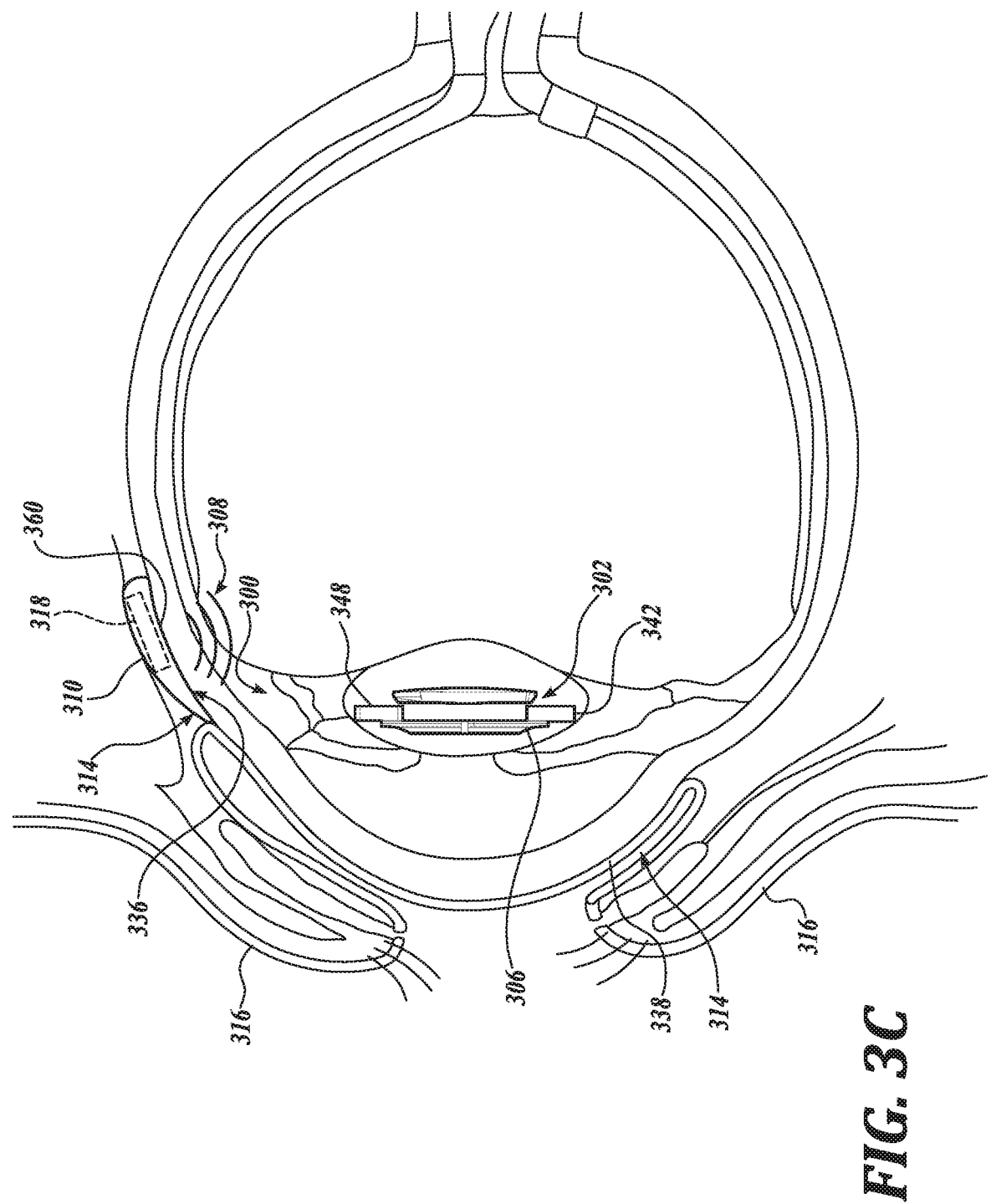
FIG. 3C is a view in cross-section of the ophthalmic system of FIG. 3A shown implanted in and mounted in an eye, in accordance with an embodiment of the disclosure.

In an embodiment, one or more sensors 144C and 144D are disposed on the extraocular device 110, as discussed further herein with respect to FIGS. 3A-3C. In an embodiment, such extraocular sensors 144C and 144D are disposed on a portion of the ring-shaped structure 122 of extraocular device 110. Such extraocular sensors 144C and 144D may be positioned to sense an angle of an eye 112 such that a viewing angle and a viewing distance may be inferred.

In an embodiment, the one or more sensors 144A-144D are further configured to generate accommodation control signals representative of the biological accommodation signals. Where sensors 144C and 144D are disposed on extraocular device 110, such accommodation control signals may be transmitted for receipt by the accommodating intraocular device 102. For example, in an embodiment, the accommodating intraocular device 102 further includes an accommodation actuator 106 configured to change an optical power of the accommodating intraocular device 102 based on the accommodation control signals. In that regard, the accommodating intraocular device may include an intraocular controller 142 operatively coupled to the wireless receiver 104, the one or more 144A-144B sensors, and the accommodation actuator 106.

The intraocular controller 142 may further include logic that when executed by the intraocular controller 142 causes the ophthalmic system 100 to perform operations including driving the accommodation actuator 106 to change the optical power of the accommodating intraocular device 102 based on the accommodation control signals. In this regard, the ophthalmic system 100 is configured to change an optical power of the ophthalmic system 100 based on a target accommodation state of the eye 112 in and on which the ophthalmic system 100 is disposed.

Figure 2A:
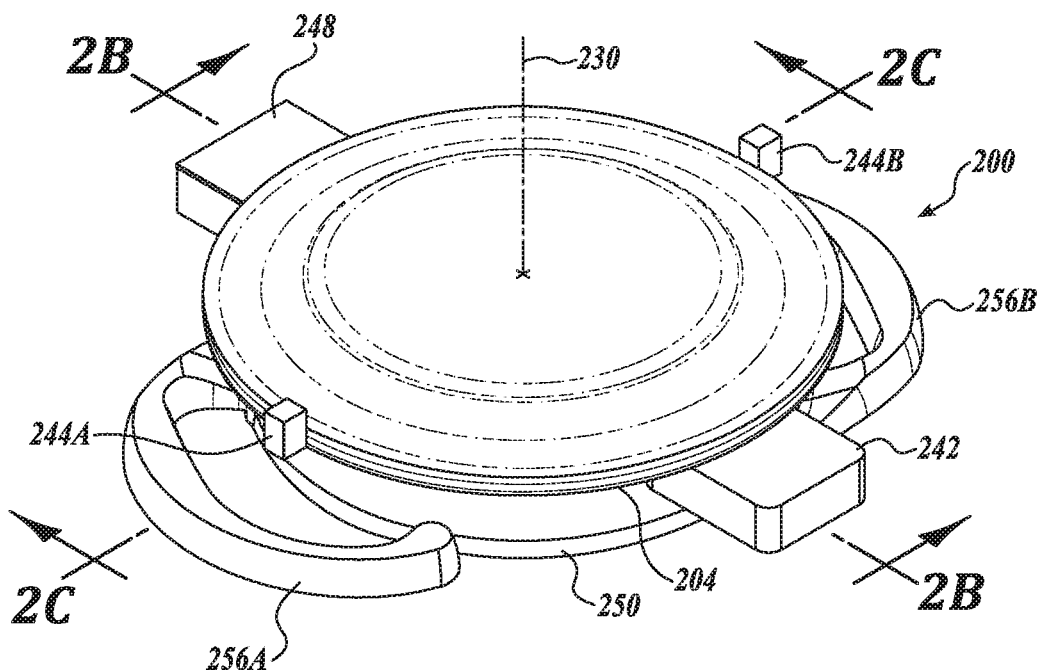
FIG. 2A is a perspective view of an accommodating intraocular device, in accordance with an embodiment of the disclosure.
Figure 2B:
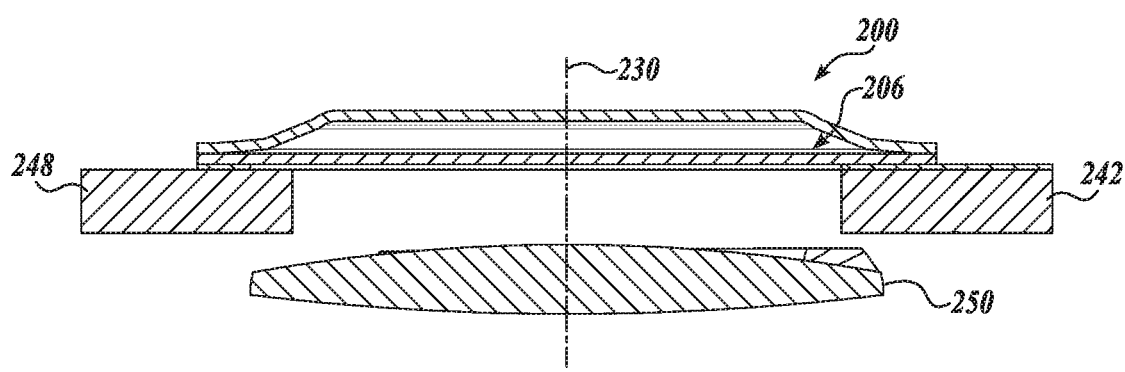
FIG. 2B is a view in cross-section of the accommodating intraocular device of FIG. 2A, in accordance with an embodiment of the disclosure.
Figure 2C:
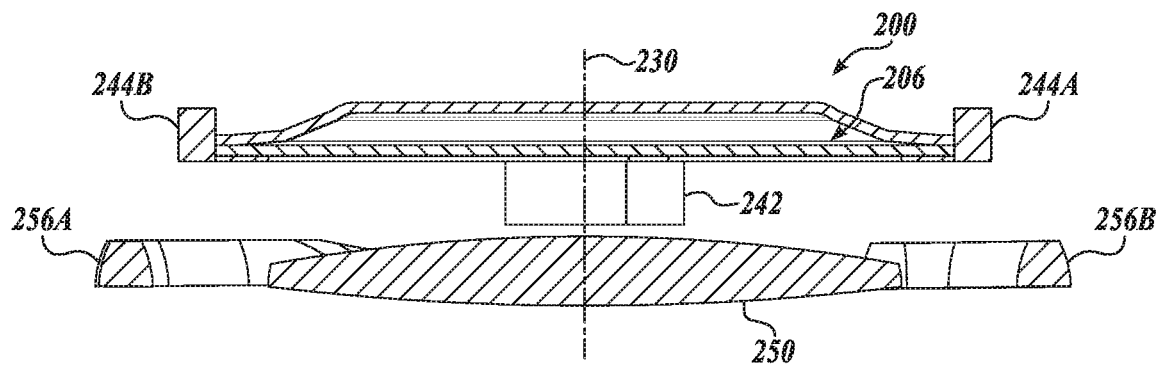
FIG. 2C is another view in cross-section of the accommodating intraocular device of FIG. 2A, in accordance with an embodiment of the disclosure.

An accommodating intraocular device, in accordance with embodiments of the present disclosure, will now be described. In that regard, attention is directed to FIGS. 2A-2C. FIG. 2A is a perspective view of an accommodating intraocular device 202, in accordance with an embodiment of the disclosure. FIG. 2B is a view in cross-section of the accommodating intraocular device 202, in accordance with an embodiment of the disclosure. FIG. 2C is another view in cross-section of the accommodating intraocular device 202, in accordance with an embodiment of the disclosure. In an embodiment, accommodating intraocular device 202 is an example of accommodating intraocular device 102.

Accommodating intraocular device 202 includes a wireless receiver 204 shown here as a circular antenna; and an accommodation actuator 206 configured to change an optical power of the accommodating intraocular device 202. Further, wireless receiver 204 is suitable to wirelessly receive power, such as radio-frequency power generated by a wireless transmitter, such as a wireless transmitter 126 of extraocular device 110 discussed further herein with respect to FIGS. 1A-1C. Accommodation actuator 206 is configured to receive power from the wireless receiver 204 suitable to drive accommodation actuator 206. In that regard, accommodation actuator 206 does not have to rely upon an intraocular power source to change an optical power of the accommodating intraocular device 202.

Accommodating intraocular device 202 may include an intraocular power source 248 operably coupled to one or more accommodating intraocular device 202 electrical components, such as an intraocular controller 242, accommodation actuator 206, wireless receiver 204, haptics 256A and 256B, sensors 244A and 244B, and the like, to provide power to such devices and to store power for later use. Particularly, the accommodating intraocular device 202 may further include an intraocular power source 248 configured to receive power from the wireless receiver 204 and to provide electrical power to the accommodation actuator 206. Such an intraocular power source 248 may include one or more capacitors, such as one or more supercapacitors. Capacitors of the intraocular power source 248, particularly supercapacitors, may be suitable to satisfy peak power requirements of the accommodating intraocular device 202.

In an embodiment, such an intraocular power source 248 does not include a battery. As discussed further herein, such intraocular batteries may fail over time requiring burdensome and invasive removal of the accommodating intraocular device 202, whereas capacitors tend to have a longer working life than batteries and may be suitable to be rolled, folded, and the like for relatively non-invasive implantation.

Accommodation actuator 206 can include any accommodation actuator 206 suitable to be intraocularly implanted and to change an optical power of intraocular device 202. Such accommodation actuators 206 can include electrowetting accommodation actuators, accommodation actuators including liquid crystals, and the like. In an embodiment, the accommodation actuator 206 is electrically actuated, such as with electrical power from intraocular power source 248, to change an optical power of the accommodating intraocular device 202.

Accommodating intraocular device 202 further includes sensors 244A and 244B configured to detect biological accommodation signals of the eye and an intraocular controller 242 operatively coupled to the wireless receiver 204, sensors 244A and 244B, and the accommodation actuator 206. In an embodiment, sensors 244A and 244B generate accommodation control signals. In an embodiment, the intraocular controller 242 includes logic that when executed by the intraocular controller 242 causes the ophthalmic system 200 to perform operations including driving the accommodation actuator 206 to change the optical power of the accommodating intraocular device 202 based on the accommodation control signals.

In the illustrated embodiment, accommodating intraocular device 202 includes a base lens 250 having a static optical power. Such a base lens 250 is suitable to provide a base optical power which may be supplemented by the accommodation actuator 206.

Accommodating intraocular device 202 may further includes haptics 256A and 256B, shown here coupled to the base lens 250, shaped to orient the accommodating intraocular device 202 within an eye. In this regard, an optical axis 230 of accommodating intraocular device 202 may be oriented with respect to an optical axis of the eye into which it is implanted and/or an extraocular device mounted to the eye.

Another ophthalmic system in accordance with an embodiment of the disclosure will now be described. In that regard, attention is directed to FIGS. 3A-3C in which the ophthalmic system 300 is illustrated. FIG. 3A is a perspective view of ophthalmic system 300, in accordance with embodiment of the disclosure. FIG. 3B is a top-down plan view of the ophthalmic system 300 shown implanted in and mounted on an eye 312, in accordance with an embodiment of the disclosure. FIG. 3C is a view in cross-section of the ophthalmic system 300 shown implanted in and mounted in an eye 312, in accordance with an embodiment of the disclosure.

Ophthalmic system 300 includes an accommodating intraocular device 302 and a remote device 310 separate from the accommodating intraocular device 302. In an embodiment, accommodating intraocular device 302 is an example of accommodating intraocular devices 102 and/or 202.

In the illustrated embodiment, the remote device 310 is an extraocular device 310 shaped to be mountable to portion 314 of the eye 312 disposed outside of a fibrous tunic of the eye 312 including the cornea and the sclera, such as surgically implanted below the conjunctiva 338. In this regard, the remote device 310 is an extraocular device 310 shaped to be mounted or implanted outside a bulb of the eye 312. As shown in FIGS. 3B and 3C, extraocular device 310 is shaped to fit under an eyelid 316, such as an upper eyelid 316 and/or a lower eyelid 316. In the illustrated embodiment, extraocular device 310 is shaped to conformably contact a surface of the eye 312, such as a surface of the sclera 360. In the illustrated embodiment, the extraocular device 310 has a semi-toroidal shape shaped to be removably mounted to a portion 314 of the eye 312 outside a fibrous tunic of the eye, such as an arc of a periocular space of the eye. In an embodiment, extraocular device 310 is shaped such that it does not extend over a pupil of an eye when removably mounted thereon. As shown, extraocular device 310 includes a scleral surface 336 shaped to conformably contact a portion of sclera 360 of the eye 312 when the extraocular device 310 is removably mounted to the portion 314 of the eye 312. In this regard, the extraocular device 310 is shaped to be removably placed proximal to accommodating intraocular device 302 implanted in an eye 312. Such proximal placement is suitable to efficiently and wirelessly transfer power 308 and signals from extraocular device 310 disposed outside of the eye 312 to accommodating intraocular device 302 implanted within the eye 312. As discussed further herein, such power 308 and signals may be used to drive an accommodation actuator 306 of accommodating intraocular device 302. Likewise, the extraocular device 310 is shaped to be removable from the portion 314 of an eye 312 by a trained surgeon, such as when the extraocular device 310 is ready to be cleaned, recharged, reprogrammed, and the like. While the extraocular device 310 is removable by a surgeon when placed under the conjunctiva 338, such removal is generally less burdensome on a patient than, for example, removing a device implanted within the eye 312.

While extraocular devices shaped to be disposed under an eyelid 316 and in a periocular space of the eye 312 are described herein, it will be understood that the extraocular devices of the present disclosure may be shaped to be removably mounted to other portions of the eye 312 outside of a bulb of the eye, such as atop the conjunctiva 338 and/or in a scleral flap of the eye 312. (Not shown). Likewise, the extraocular device may include a contact lens. (Not shown). Such a contact lens may have an optical power suitable to correct any deviations that occur from, for example, mismatch between targeted and actual optical power of the accommodating intraocular device 302, optical power drift of the accommodating intraocular device 302 over time, and change in patient's eye shape over time.

Extraocular device 310 further includes an extraocular power source 318 and a wireless transmitter 320 operatively coupled to the extraocular power source 318 and configured to wirelessly transmit power 308 from the extraocular power source 318 for receipt by a wireless receiver 304 of the accommodating intraocular device 302. As shown, extraocular power source 318 is disposed in housing 334 of the extraocular device 310. Wireless transmitter is shown to encircle a periphery 340 of housing 334 of the extraocular device 310. Such wireless power 308 and signal can take the form of radio-frequency electromagnetic radiation emitted from an extraocular antenna of the wireless transmitter 320. Wireless transmitter 320 is suitable to provide power 308 and signals in the form of, for example, radio-frequency power 308 and signals for receipt by wireless receiver 304 of accommodating intraocular device 302. As discussed further herein, such power 308 and signals may be used to drive accommodation actuator 306 of accommodating intraocular device 302.

In an embodiment, the extraocular device 310 includes one or more sensors 344C and 344D configured to detect biological accommodation signals of the eye 312 and to generate accommodation control signals representative of the biological accommodation signals. In this regard, the extraocular device 310 may further include an extraocular controller 346, shown here disposed in the housing 334, including logic that when executed by the extraocular controller 346 causes the ophthalmic system 300 to perform operations including transmitting, with the wireless transmitter 320, the accommodation control signals for receipt by the wireless receiver 304. Accordingly, a sensor 344C and 344D having relatively high power requirements may be disposed in the extraocular device 310 and yet transmit the accommodation control signals to the accommodating intraocular device 302 to change an optical power of the ophthalmic system 300.

As shown, electrical components including sensors 344C and 344D, extraocular power source 318, wireless transmitter 320, and extraocular controller 346 are in conductive communication through traces 358.

Accommodating intraocular device 302 is shown to include a wireless receiver 304; and an accommodation actuator 306 configured to change an optical power of the accommodating intraocular device 302. In an embodiment, accommodating intraocular device 302 is an example of accommodating intraocular devices 102 and/or 202. As discussed further herein, the accommodation actuator 306 is configured to receive power 308 from the wireless receiver 304 suitable to drive the accommodation actuator 306 to change an optical power of the accommodating intraocular device 302. The accommodating intraocular device 302 may further include sensors 344A and 344B configured to detect biological accommodation signals of the eye 312 and to generate accommodation control signals representative of the biological accommodation signals. As shown, the accommodating intraocular device 302 further includes an intraocular controller 342 operatively coupled to the wireless receiver 304, the sensors 344A and 344B, and the accommodation actuator 306. As discussed further herein with respect to FIGS. 1A-1C, intraocular controller 342 may include logic that when executed by the intraocular controller 342 causes the ophthalmic system 300 to perform operations including driving the accommodation actuator 306 to change the optical power of the accommodating intraocular device 302 based on the accommodation control signals.

Accommodating intraocular device 302 is shown to further include a base lens 350 having a static optical power. Such a base lens 350 is suitable to provide a base optical power which may be supplemented by the accommodation actuator 306.

Accommodating intraocular device 302 may further includes haptics 356A and 356B shaped to orient the accommodating intraocular device 302 within an eye 312. In this regard, an optical axis 330 of accommodating intraocular device 302 may be oriented with respect to an optical axis of the eye 312 into which the accommodating intraocular device 302 is implanted and on which the extraocular device 310 is mounted.

Figure 4:
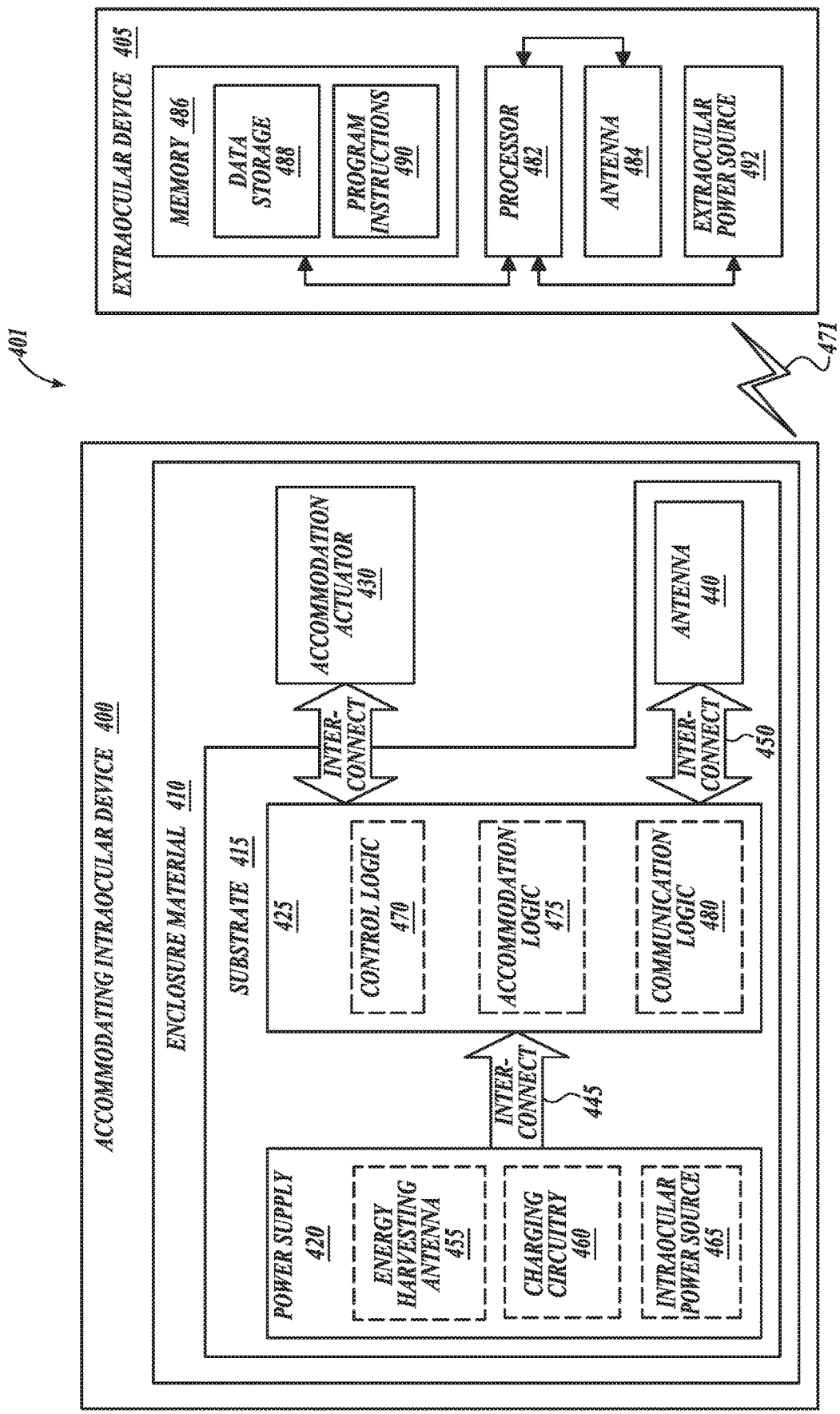
FIG. 4 is a schematic block diagram of another ophthalmic system, in accordance with an embodiment of the disclosure.

FIG. 4 is schematic block diagram of an ophthalmic system 401, in accordance with an embodiment of the disclosure. Ophthalmic system 401 includes an accommodating intraocular device 400 and extraocular device 405. In an embodiment, ophthalmic system 401 is an example of ophthalmic systems 100 and/or 300. In an embodiment, accommodating intraocular device 400 is an example of accommodating intraocular devices 102, 202, and/or 302.

Accommodating intraocular device 400 may be an implantable device shaped to be implantable in an eye. In the depicted embodiment, accommodating intraocular device 400 includes an enclosure material 410, such as a hydrogel, formed to be implanted into an eye. A substrate 415 is embedded within or surrounded by enclosure material 410 to provide a mounting surface for a power supply 420, a controller 425, an antenna 440, and various interconnects 445 and 450. The substrate 415 and the associated electronics may be one implementation of the intraocular controller 142. The illustrated embodiment of power supply 420 includes an energy harvesting antenna 455, charging circuitry 460, and an intraocular power source 465. The illustrated embodiment of controller 425 includes control logic 470, accommodation logic 475, and communication logic 480. As shown, accommodation actuator 430 is disposed in the enclosure material 410.

Power supply 420 supplies operating voltages to the controller 425 and/or the accommodation actuator 430. Antenna 440 is operated by the controller 425 to communicate information to and/or from accommodating intraocular device 400. In an embodiment, antenna 440 is an example of the wireless receivers discussed further herein with respect to FIGS. 1A-1C, 2A-2C, and 3A-3C. In the illustrated embodiment, antenna 440, controller 425, and power supply 420 are disposed on/in substrate 415, while accommodation actuator 430 is disposed in enclosure material 410 (not in/on substrate 415). However, in other embodiments, the various pieces of circuitry and devices contained in accommodating intraocular device 400 may be disposed in/on substrate 415 or in enclosure material 410, depending on the specific design of accommodating intraocular device 400. For example, in one embodiment, accommodation actuator 430 may be disposed on a transparent substrate.

Substrate 415 includes one or more surfaces suitable for mounting controller 425, power supply 420, and antenna 440. Substrate 415 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 415 to form circuitry, electrodes, etc. For example, antenna 440 can be formed by depositing a pattern of gold or another conductive material on substrate 415. Similarly, interconnects 445 and 450 can be formed by depositing suitable patterns of conductive materials on substrate 415. A combination of resists, masks, and deposition techniques can be employed to pattern materials on substrate 415. Substrate 415 can be a relatively rigid material, such as polyethylene terephthalate ("PET") or another material sufficient to structurally support the circuitry and/or electronics within enclosure material 410. Accommodating intraocular device 400 can alternatively be arranged with a group of unconnected substrates rather than a single substrate 415. For example, controller 425 and power supply 420 can be mounted to one substrate 415, while antenna 440 is mounted to another substrate 415 and the two can be electrically connected via interconnects. Substrate 415 may also be a continuous piece of semiconductor, housing all or some of the aforementioned pieces of device architecture as integrated circuitry.

Substrate 415 can be shaped as a flattened ring with a radial width dimension sufficient to provide a mounting platform for the embedded electronic components. Substrate 415 can have a thickness sufficiently small to allow substrate 415 to be embedded in enclosure material 410 without adversely influencing the profile of accommodating intraocular device 400. Substrate 415 can have a thickness sufficiently large to provide structural stability suitable for supporting the electronics mounted thereon. For example, substrate 415 can be shaped as a ring with a diameter of about 10 millimeters, a radial width of about 1 millimeter (e.g., an outer radius 1 millimeter larger than an inner radius), and a thickness of about 50 micrometers.

In the illustrated embodiment, power supply 420 includes intraocular power source 465 to power the various embedded electronics, including controller 425. Intraocular power source 465 may be inductively charged by charging circuitry 460 and energy harvesting antenna 455. In one embodiment, the intraocular power source 465 includes one of more capacitors, such as one or more supercapacitors. In one embodiment, antenna 440 and energy harvesting antenna 455 are independent antennae, which serve their respective functions of energy harvesting and communications. In another embodiment, energy harvesting antenna 455 and antenna 440 are the same physical antenna that are time shared for their respective functions of inductive charging and wireless communications with extraocular device 405. Additionally or alternatively, power supply 420 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 460 may include a rectifier/regulator to condition the captured energy for charging intraocular power source 465 or directly power controller 425 without intraocular power source 465. Charging circuitry 460 may also include one or more energy storage devices to mitigate high frequency variations in energy harvesting antenna 455. For example, one or more energy storage devices (e.g., a capacitor, an inductor, etc.) can be connected to function as a low-pass filter.

Controller 425 contains logic to choreograph the operation of the other embedded components. Control logic 470 controls the general operation of accommodating intraocular device 400, including providing a logical user interface, power control functionality, etc. Accommodation logic 475 includes logic for receiving signals from sensors monitoring the orientation of the eye, determining the current gaze direction, position or displacement of ciliary muscles of the eye, electrical activity of the eye, or focal distance of the user, and manipulating accommodation actuator 430 (focal distance of the intraocular device 402) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 480 provides communication protocols for wireless communication with extraocular device 405 via antenna 440. In one embodiment, communication logic 480 provides backscatter communication via antenna 440 when in the presence of an electromagnetic field 471 output from extraocular device 405. In one embodiment, communication logic 480 operates as a smart wireless radio-frequency identification ("RFD") tag that modulates the impedance of antenna 440 for backscatter wireless communications. The various logic modules of controller 425 may be implemented in software/firmware executed on a general purpose microprocessor, in hardware (e.g., application specific integrated circuit), or a combination of both.

Accommodating intraocular device 400 may include various other embedded electronics and logic modules. For example, a light source or pixel array may be included to provide visible feedback to the user. An accelerometer or gyroscope may be included to provide positional, rotational, directional or acceleration feedback information to controller 425.

The illustrated embodiment also includes extraocular device 405 with a processor 482, an antenna 484, extraocular power source 492, and memory 486. Memory 486 in extraocular device 405 includes data storage 488 and program instructions 490. As shown extraocular device 405 is separate from accommodating intraocular device 400 (see also FIGS. 1A-1C), but may be placed in its proximity to charge accommodating intraocular device 400, send instructions to accommodating intraocular device 400, and/or extract data from accommodating intraocular device 400. In one embodiment, extraocular device 405 may resemble a conventional contact lens. In another embodiment, extraocular device 405 comprises a ring-shaped structure shaped to encircle a periocular space of the eye when the extraocular device 405 is removably mounted to the underlid portion of the eye, as discussed further herein with respect to FIGS. 1A-1C. In one embodiment, the extraocular device 405 is semi-toroidal and shaped to conformably contact a portion of the sclera of the eye when the extraocular device 405 is removably mounted to a portion of the eye outside a bulb of the eye as discussed further herein with respect to FIGS. 3A-3C.

External extraocular device 405 includes an antenna 484 (or group of more than one antennae) to send and receive wireless signals 471 to and from accommodating intraocular device 400. External extraocular device 405 also includes a computing system with a processor 482 in communication with a memory 486. Memory 486 is a non-transitory computer-readable medium that can include, without limitation, magnetic disks, optical disks, organic memory, and/or any other volatile (e.g., RAM) or non-volatile (e.g., ROM) storage system readable by the extraocular controller 146. Memory 486 can include a data storage 488 to store indications of data, such as data logs (e.g., user logs), program settings (e.g., to adjust behavior of accommodating intraocular device 400 and/or extraocular device 405), etc. Memory 486 can also include program instructions 490 for execution by processor 482 to cause the extraocular device 405 to perform processes specified by the instructions 490. For example, program instructions 490 can cause extraocular device 405 to provide a user interface that allows for retrieving information communicated from accommodating intraocular device 400 or allows transmitting information to accommodating intraocular device 400 to program or otherwise select operational modes of accommodating intraocular device 400. Extraocular device 405 can also include one or more hardware components for operating antenna 484 to send and receive wireless signals 471 to and from accommodating intraocular device 400.

Extraocular device 405 can provide wireless connectivity sufficient to provide the wireless communication link 471. In some instances, extraocular device 405 is configured to be worn or mounted relatively near a wearer's eye and the accommodating intraocular device 400 implanted therein to allow the wireless communication link 471 to operate with a low power budget.

Figure 5:
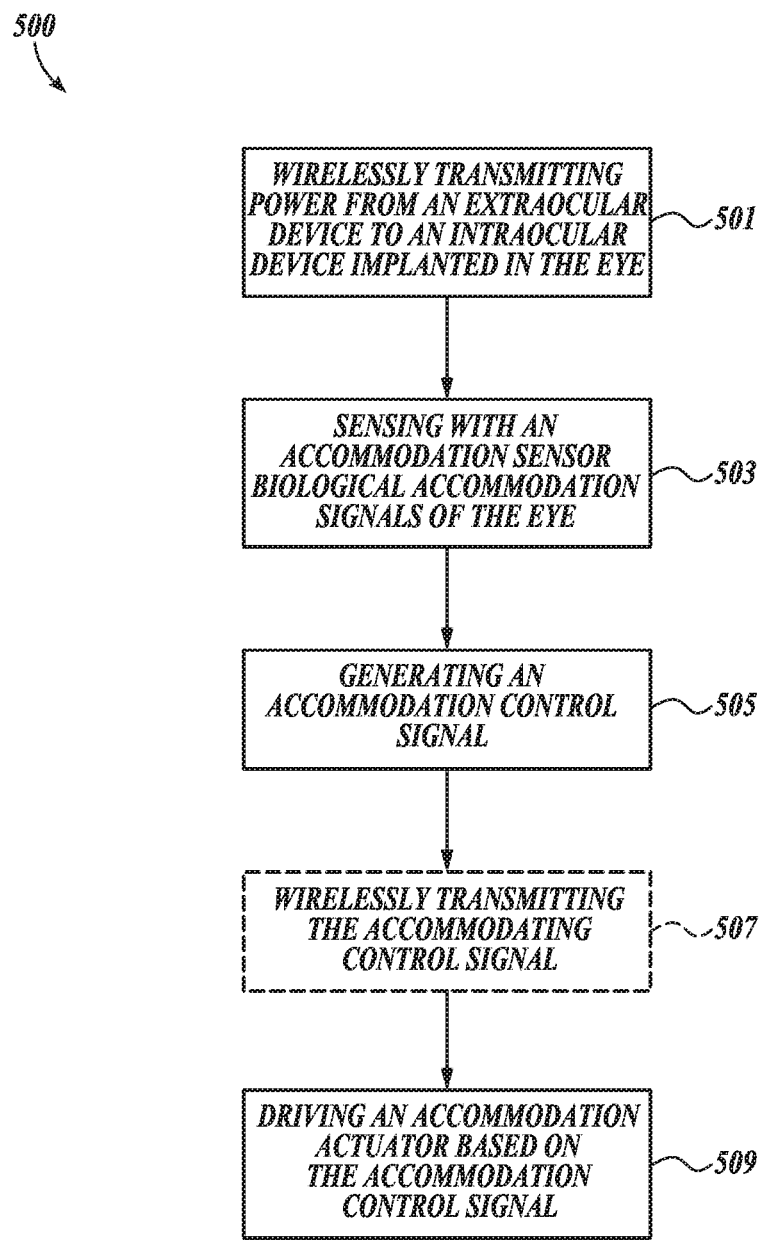
FIG. 5 is a block diagram of a method of changing an optical power of an ophthalmic system, in accordance with an embodiment of the disclosure.

A method of changing an optical power of an ophthalmic system in accordance with an embodiment of the disclosure will now be described. In that regard, attention is directed to FIG. 5 in which a block diagram of a method 500, in accordance with an embodiment of the disclosure, is illustrated. Method 500 may be used, for example, to change an optical power of ophthalmic systems 100 and/or 300 and to change an optical power of accommodating intraocular device 202 in conjunction with an extraocular device in accordance with embodiments of the disclosure.

Method 500 may begin with process block 501, which includes wirelessly transmitting power from a power source of remote device, such as an extraocular device, removably mounted outside a bulb of an eye to an accommodating intraocular device implanted in the eye. Such power may include radio-frequency or other electromagnetic radiation, such as radio-frequency electromagnetic radiation emitted from a wireless transmitter of the extraocular device. While radio-frequency electromagnetic radiation is discussed herein, it will be understood that other types of wireless power, such as optical power, transient electrical signals sent through body tissue, ultrasonic waves, and the like, are encompassed by the methods of the present disclosure.

The extraocular device is removably mounted to a portion of the eye outside of a bulb of the eye, such as disposed under an eyelid. Such removable mounting may include mounting the extraocular device to a periocular space of the eye (see FIGS. 1C and 1D), under an eyelid and in contact with conjunctiva of the eye (see FIGS. 3B and 3C), underneath conjunctiva of the eye, and/or in a scleral flap of the eye. In this regard, the extraocular device may be mounted to and removed from an eye without, for example, a surgical or other invasive procedure, such as by a user of the ophthalmic system and without assistance from a healthcare provider. Further, because the extraocular device is disposed under a lid of the eye, the extraocular device is securely but removably disposed proximate to the accommodating intraocular device implanted in the eye.

In an embodiment, transmitting power from the power source of the extraocular device to the accommodating intraocular device includes transmitting power with a wireless transmitter of the extraocular device for receipt by a wireless receiver of the accommodating intraocular device. As discussed further herein with respect to FIGS. 1A-1C, power may be wirelessly transmitted from an antenna of the extraocular device and received by an antenna of the accommodating intraocular device. In an embodiment, wirelessly transmitting power includes wirelessly transmitting power with a ring-shaped wireless transmitter of the extraocular device that encircles a periocular space of the eye, as shown in FIGS. 1C and 1D. As shown in FIGS. 1C and 1D, a central axis of an antenna of the wireless transmitter may be positioned coaxially with a central axis of an antenna of the wireless receiver. In such a configuration, the ring-shaped wireless transmitter is shaped and positioned to efficiently effect wireless transmission of power and, in certain embodiments, signals from the extraocular device to the accommodating intraocular device. In an embodiment, the extraocular device semi-toroidally shaped to conformably contact a portion of conjunctiva of the eye when the extraocular device is removably mounted to a portion of the eye outside a bulb of the eye, as discussed further herein with respect to FIGS. 3A-3C.

As noted further herein, accommodating intraocular device is implanted within the eye. In an embodiment, the accommodating intraocular device is implanted in a capsular bag of the eye. The accommodating intraocular device may be disposed within the lens capsule of the eye. In this regard, the accommodating intraocular device is disposed proximate to the extraocular device suitable for efficient wireless transfer of power and signals.

Process block 501 may be followed by process block 503, which includes sensing with an accommodation sensor biological accommodation signals of the eye. Such an accommodation sensor can include an ultrasound transducer, such as a lead ziconate titanate or other piezoelectric device, configured to generate ultrasound. In an embodiment, sensing includes sensing with two or more such ultrasound transducers disposed, for example in two more different positions of the accommodating intraocular device or the extraocular device. In that regard, the two or more sensors are configured, for example, to sense a position of the ciliary muscles on different sides of the eye.

In an embodiment, the sensor is configured to sense a distance of an object in the user's direction of gaze. Such a sensor can include a light or other phased signal transmitter and receptor configured to detect a phase shift in the phased signal and/or time of flight of the light or other phased signal between the emitter and the receptor.

In an embodiment, the sensor can include an electromyography sensor configured to sense electrical activity of the ciliary muscles of the eye.

In an embodiment, sensing includes sensing with sensors disposed on the accommodating intraocular device. In an embodiment, sensing includes sensing in the extraocular device. In that regard, sensors having relatively high power requirements, such as time-of-flight sensors, may be directly powered by an extraocular power source. Such a power source disposed in and powered by the extraocular avoids relying on a power source disposed in the accommodating intraocular device. As discussed further herein, power sources of accommodating intraocular devices, such as batteries, may fail over time and add bulk to such devices requiring more invasive and burdensome implantation and removal procedures for the patient. By disposing components of the ophthalmic system with relatively high power requirements, such as sensors, in the extraocular device the intraocular device may avoid using a battery and the attendant challenges associated with intraocular batteries.

Process block 503 may be followed by process block 505, which includes generating accommodation control signals representative of the biological accommodation signals. As above, sensing can include emitting one or more ultrasound sources to ciliary muscles of the eye. Ultrasound reflected off of the ciliary muscles may be used, for example, to generate accommodation control signals, such as signals representative of, for example, a position and/or a velocity of the ciliary muscles. Additionally, in some embodiments, sensing includes sensing electrical activity of ciliary muscles of the eye. Such electrical activity may be used to generate the accommodation control signals representative of electrical activity of the ciliary muscles.

Where sensing includes sensing with sensors disposed on the extraocular device, process block 503 may followed by process block 505, which includes wirelessly transmitting the accommodating control signals to the accommodating intraocular device. In this regard, and as discussed further herein with respect to process block 507, the accommodating control signals are available to the accommodating intraocular device, for example, to inform and direct driving an accommodation actuator disposed therein. In an embodiment, process block 505 is optional.

Process blocks 505 and 507 may be followed by process block 509, which includes driving an accommodation actuator disposed in the accommodating intraocular device based on the accommodation control signals to change an optical power of the ophthalmic system. In an embodiment, driving the accommodation actuator includes electrically driving the accommodation actuator. In an embodiment, the accommodation actuator is an electrowetting accommodation actuator. While electrowetting accommodation actuators are discussed herein, it will be understood that other accommodation actuators are encompassed by method 500.

As above, driving the accommodation actuator includes driving the accommodation actuator based upon the accommodation control signals. In that regard, the accommodation actuator is driven to change the optical power of the accommodating intraocular device to reflect a target accommodation state of the eye and based upon the biological accommodation signals.

The order in which some or all of the process blocks appear in each process should not be deemed limiting. Rather, one of ordinary skill in the art having the benefit of the present disclosure will understand that some of the process blocks may be executed in a variety of orders not illustrated, or even in parallel.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic system comprising:
    an accommodating intraocular device shaped to be implantable in an eye, the accommodating intraocular device comprising:
        a wireless receiver; and
        an accommodation actuator configured to receive power from the wireless receiver and to change an optical power of the accommodating intraocular device; and
    a remote device separate from the accommodating intraocular device and shaped to be removably mountable to portion of the eye disposed outside of a bulb of the eye, the remote device comprising:
        a power source; and
        a wireless transmitter operatively coupled to the power source and configured to wirelessly transmit power from the power source to the wireless receiver of the accommodating intraocular device,
        wherein the remote device is semi-toroidally shaped to conformably contact and be removably mounted to a portion of the eye outside a fibrous tunic of the eye, and
        wherein the remote device is shaped to be implanted under conjunctiva of the eye and contact a portion of sclera of the eye when the remote device is implanted under the conjunctiva.

2. The ophthalmic system of claim 1, wherein the wireless transmitter encircles a periphery of a housing of the remote device.

3. The ophthalmic system of claim 1, further comprising a sensor configured to detect biological accommodation signals of the eye and to generate accommodation control signals representative of the biological accommodation signals.

4. The ophthalmic system of claim 3, wherein the accommodating intraocular device further comprises an intraocular controller operatively coupled to the wireless receiver, the sensor, and the accommodation actuator, the intraocular controller including logic that when executed by the intraocular controller causes the ophthalmic system to perform operations including:

driving the accommodation actuator to change the optical power of the accommodating intraocular device based on the accommodation control signals.

5. The ophthalmic system of claim 3, wherein the sensor is disposed on the remote device.

6. The ophthalmic system of claim 5, wherein the remote device further comprises a controller operatively coupled to the sensor, the power source, and the wireless transmitter and including logic that when executed by the controller causes the ophthalmic system to perform operations including:

transmitting, with the wireless transmitter, the accommodation control signals for receipt by the wireless receiver.

7. The ophthalmic system of claim 3, wherein the accommodation control signals include a signal based on a position of ciliary muscles of the eye.

8. The ophthalmic system of claim 3, wherein the accommodation control signals include a signal based on electrical activity of ciliary muscles of the eye.

9. The ophthalmic system of claim 1, wherein the accommodating intraocular device further comprises an intraocular power source configured to receive power from the wireless receiver and to provide electrical power to the accommodation actuator.

10. The ophthalmic system of claim 9, wherein the intraocular power source comprises one or more capacitors.

\* \* \* \* \*

UNITED STATES PATENT AND TRADEMARK OFFICE
CERTIFICATE OF CORRECTION

PATENT NO. : 11,311,373 B2
APPLICATION NO. : 16/670921
DATED : April 26, 2022
INVENTOR(S) : C. Gutierrez et al.

Page 1 of 1

It is certified that error appears in the above-identified patent and that said Letters Patent is hereby corrected as shown below:

In the Claims

| Column | Line | |
|--------|------|---|
| 16 | 42 | change "to portion" to -- to a portion -- |

Signed and Sealed this
Twenty-third Day of May, 2023

Katherine Kelly Vidal
*Director of the United States Patent and Trademark Office*